(12) United States Patent
Fotinos

(10) Patent No.: US 6,410,048 B1
(45) Date of Patent: *Jun. 25, 2002

(54) PROLAMIN-PLANT POLAR LIPID COMBINATION, PREPARATION METHOD AND APPLICATIONS

(75) Inventor: Spiros Fotinos, Athens (GR)

(73) Assignee: Laboratories Lavipharm S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/554,486

(22) PCT Filed: Nov. 10, 1998

(86) PCT No.: PCT/FR98/02400

§ 371 (c)(1), (2), (4) Date: Jul. 18, 2000

(87) PCT Pub. No.: WO99/25326

PCT Pub. Date: May 27, 1999

(30) Foreign Application Priority Data

Nov. 13, 1997 (FR) .............................. 97 14242

(51) Int. Cl.[7] .............................. A61L 15/44

(52) U.S. Cl. ..................... 424/447; 424/401; 424/443; 424/448; 424/449; 424/725

(58) Field of Search ............................... 424/401, 443, 424/447, 448, 195.1, 449, 725

(56) References Cited

U.S. PATENT DOCUMENTS 6,045,809 A * 4/2000 Postaire et al. ............. 424/400

* cited by examiner

Primary Examiner—Jose Dees
Assistant Examiner—Konata M. George
(74) Attorney, Agent, or Firm—Dechert

(57) ABSTRACT

The invention provides a prolamine-plant polar lipid association, wherein the prolamine and plant polar lipid components are present in such proportions so that stable films can be obtained with this association, which is preferably in the form of a hydro-alcoholic gel comprising: 20–40% w/w of prolamines, preferably gliadin; 0.1–5% w/w of ceramides, preferably wheat ceramides; hydro-ethanolic solution (35 to 80°) ad 100%.

This association may be used for preparing films, patches, aerosols for use in the delivery of active substances such as therapeutic and cosmetic agents.

28 Claims, 2 Drawing Sheets

PROLAMIN-PLANT POLAR LIPID COMBINATION, PREPARATION METHOD AND APPLICATIONS

BACKGROUND OF THE INVENTION

1. Field of the Invention

The present invention relates to an association of plant proteins and plant polar lipids, preferably to an association of cereal proteins and cereal polar lipids and more preferably to an association of wheat prolamines and wheat polar lipids, for use in the delivery of active substances, including therapeutic and cosmetic agents, to humans.

2. Description of the Prior Art

Carrier systems for a variety of active substances including drugs, hormones, peptides, glycopeptides, growth factors and the like are well recognized in the art to be made of synthetic polymers.

Such systems particularly employed for delivering active agents to the skin for protection and renewal, or to the wound for healing and hemostasis, or further in the form of a device for dermal, transdermal, mucosal and transmucosal administration, should satisfy requirements such as:

to be non-toxic, to not interrupt the delivery of an active substance to the application site and to not interfere with the rate of release of the active substance, to not cause irritation, to be removed easily without discomfort, when needed, to not deteriorate, peel or loosen over the period of application, and moreover, to not leave a residue upon removal, when especially applied onto the skin.

Natural polymers, namely collagen and gelatin, have also been used as encapsulating agents, carriers, supporting agents, dispensers, etc., for delivering active agents.

Collagen, a biodegradable polymer found in man, has been used for the preparation of a patch employed in visceral surgery as disclosed in U.S. Pat. No. 5,201,745, the preparation of a pad for promoting hemostasis, treating traumatized tissues or expediting tissue suture as taught in WO-A-93/10731.

Similarly, collagen membranes have been used for delivering active substances as disclosed in EP-A-0 621 044, while collagen films were proposed to improve controlled drug delivery as described in WO-A-95/28964 and EP-A-0 518 697.

Chitin, another biopolymer abundant in crustaceans, has been proposed for achieving hemostasis as disclosed in U.S. Pat. No. 4,394,373 and for the preparation of corneal bandages and contact lenses in EP-A-0 486 294. Chitin and chitosan, its deacetylated product, have been proposed for the preparation of sustained release formulations as described in EP-A-0 187 703.

In general, polymers of natural origin as those given above, can not be considered as lacking any undesirable effect, especially those associated with an induction of an immune response. For instance, the antigenicity of collagen mainly depends on the animal species, so that there is always a need of sophisticated processing methods which could yield a least antigenic collagen. Similarly, products of marine shells are also implicated in inducing allergy to humans. Furthermore, recent evidence relates the transmission of diseases primarily originated in animal species to the humans after using/consuming animal products.

Therefore, there is a need for a natural polymer, pure and safe depriving any antigenic property, which can further be employed as a carrier system for active compounds.

SUMMARY OF THE INVENTION

The present invention uses such a natural polymer in the form of a new association of proteins and polar lipids all of plant origin, preferably an assocation of cereal proteins and plant polar lipids and more preferably an assocation of prolamines and cereal polar lipids.

Furthermore, the invention relates to the use of such an association as a carrier system in the form of a film or a patch for dermal (topical), transdermal, mucosal, transmucosal application, and also for skin healing and protection, wound healing and hemostasis.

The invention also refers to a carrier system in the form of a film or a patch further comprising active compounds and other additives which optimize the system's properties.

The invention mainly refers to the use of a natural polymer, preferably made of a prolamine protein from corn or wheat, i.e. zein or gliadin, respectively. In the present invention, gliadin is preferred but no limitation in using other prolamines or a mixture thereof is considered.

The invention also refers to the use of polar lipids of plant origin, preferably to the use of plant ceramides or polar lipid compositions rich in plant ceramides. In the present invention, plant ceramides and in particular cereal ceramides (glycosylated or not, or a mixture thereof) are preferred but no limitation in using other plant lipids or a mixture thereof is considered.

The invention also refers to the use of a particular gliadin fraction, selected as to optimize the physicochemical properties of the said polymer and further to improve its efficacy as a carrier system.

The invention preferably refers to a new gliadin-plant ceramides association used as a carrier system for the delivery of active substances to humans by dermal, transdermal, mucosal and transmucosal administration and also as a carrier system for skin protection and healing, wound healing and hemostasis.

The term "active substances" as used herein includes any therapeutic or cosmetic agent.

Furthermore, the term "therapeutic agent" as used herein includes any inorganic or organic compound without limitation, with both hydrophilic and hydrophobic properties, known in the art to be used for the treatment of certain disorders.

Moreover, the term "cosmetic agent" as used herein, includes any compound known in the art to be used for improving skin appearance.

The invention still refers to a carrier system in the form of a film or a patch adapted/adjusted in multi-shape and -size suitable for its application onto a selected site. The term "selected site" as used herein, means any part of the skin or mucosa.

The invention yet refers to a prolamine-plant polar lipid association, more particularly to a gliadin-cereal ceramide association in the form of a film or a patch used as a drug carrier system, capable of administering the active substances systemically or topically.

The terms "systemically" and "topically" as used herein, mean that the active substances will reach or not the systemic circulation, respectively.

The invention yet still refers to a prolamine-cereal polar lipid association, more particularly to a gliadin-cereal ceramide association, particularly in the form of a patch, for direct application onto the skin.

The invention yet further refers to a prolamine-cereal polar lipid association, more particularly to a gliadin-cereal ceramide association, particularly in the form of a patch wherein the said association is sandwiched between a backing film and a removable layer.

The invention yet further refers to a prolamine-cereal polar lipid association, more particularly to a gliadin-cereal ceramide association, particularly in the form of a film, the formation of which being achieved in situ onto the skin or by an appropriate processing.

The invention yet also refers to a prolamine-cereal polar lipid association, more particularly to a gliadin-cereal ceramide association in the form of a film or a patch used as a drug carrier system applied, without limitation to those applications, for transdermal delivery of drugs, or delivery of cosmetically active agents, or delivery of topically active agents such as those for treating dermal and nail diseases and pain relievers such as for treating arthritis, or delivery of buccally active agents such as those applied for pre- and post-dental operations, dental hygiene and for systemic treatment of various diseases through the mouth mucosa, or delivery of active agents through vaginal, nasal and ocular mucosa.

The invention yet still refers to a prolamine-cereal polar lipid association, more particularly to a gliadin-cereal ceramide association in the form of a film or a patch used as a drug carrier system applied, without limitation, for the delivery of drugs for skin protection and healing, wound healing and hemostasis.

The invention also refers to a prolamine-cereal polar lipid association, more particularly to a gliadin-cereal ceramide association in the form of a film or a patch for topical or transdermal drug delivery, which is easily produced and is stable for a desirable time length and safe to be worn by humans.

The term "stable" as used herein, means that, during storage, any chemical changes that may occur will not affect its therapeutic efficacy before the expiration of a predetermined time.

The term "safe" as used herein, means that no undesirable effects are induced upon its application to humans.

BRIEF DESCRIPTION OF THE DRAWINGS

FIG. 7a shows the perforation lines 9 engraved in the middle of the device space, while the scoring lines 8 are engraved horizontally. A rigid card forms the release liner, the gliadin and ceramide dispersion forms the adhesive matrix and the backing layer is formed from a flexible material. A treatment regimen might include the use in tandem of all patches.

FIG. 7b shows a set of circular patches in which the release liner is gravure coated with a synthetic adhesive layer 4b of DuroTak 72-8661.

STATEMENT OF THE INVENTION

Figure 1:
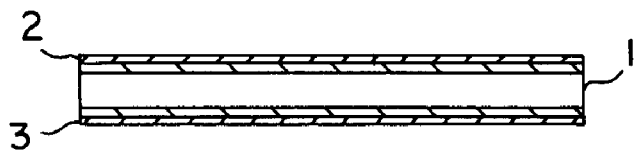
FIGS. 1–6 representing different types of patches which can incorporate the prolamine-plant polar lipid association according to the present invention, are described in the chapter named STATEMENT OF THE INVENTION, in relation to an embodiment of the invention.

According to one of its aspects, the present invention provides a prolamine-plant polar lipid association, wherein the prolamine and plant polar lipid components are present in such proportions so that stable films can be obtained with this association.

Prolamines are storage proteins of cereals, the polypeptides of which are soluble in hydro-alcoholic solutions (50–60% n-propanol or 60–90% ethanol). These proteins are found in abundance in cereals. They are hydrophobic and lipid-binding and can also interact with hydrophilic molecules. Among the most common prolamines are gliadins from wheat, zeins from corn, and hordeins from barley. They are rich in glutamine and proline, and low in basic amino acids. All of these proteins show a high degree of sequence homology.

Significant information exists in the literature with regard to the applications of such proteins. For instance, prolamine coatings for granules, tablets, nutritives etc. are disclosed in U.S. Pat. Nos. 5,160,742, 5,182,130, EP-A-0 090 559, WO-A-96/21462 and WO-A-93/12771. Moreover, prolamine films have been used in sustained release formulations of drugs as described in U.S. Pat. No. 4,137,300 and by Stella et al. in Int. J. Pharmaceutics 121, 117–121, 1995.

In the present invention, gliadin from wheat is preferred but other prolamines, without limitations, or mixtures thereof can be used.

Cereal polar lipids as extracted from cereals comprise glycolipids, phospholipids, sphingolipids known as ceramides and glycosylceramides, and low amounts of proteins and apolar lipids.

According to a preferred embodiment, the invention provides a hydro-alcoholic gel formulation, which has the following composition:

prolamines: from 20 to 40% w/w;

plant polar lipids: from 0.1 to 5% w/w;

hydro-ethanolic solution (35 to 80°): ad 100%.

According to a more peferred embodiment, the prolamines are wheat prolamines, namely gliadins.

The term "gliadin" as used in the art, represents a mixture of relatively low molecular weight proteins, classified in four groups as $\alpha$-, $\beta$-, $\gamma$- and $\omega$-gliadins according to their electrophoretic mobility, i.e. as fast to slow migrating proteins. Gliadins are rich in glutamine and proline amino acids but contain less amounts of lysine, methionine and tryptophane. In particular, $\omega$-gliadin contains the highest amount of glutamine and proline, while being poor in sulphur-containing amino acids such as methionine and cysteine.

Gliadins in solution and particularly in hydroalcoholic solution, exhibit a configuration that expedites interactions with both hydrophobic and hydrophilic molecules. Further, gliadins form a viscous solution, which, under processing, can be transformed to a film. Moreover, a dry gliadin film restores its elastomeric properties upon hydration.

Gliadins, in the form of a film, have already been proposed as carriers for the sustained delivery of drugs.

According to a particularly preferred embodiment, wheat prolamines or gliadins used in the present invention, in the form of a beige powder, have the following composition (w/w):

prolamines: 75 to 90%;

lipids: 1 to 4%;

sugars: 3 to 6%;g sulphur ashes: 2 to 5%;

moisture: 5 to 10%.

According to another preferred embodiment, the plant polar lipids contain a high proportion of ceramides and glycosylceramides, hereafter "(glycosyl)ceramides" and are preferably in the form of products extracted from a cereal fraction, preferably a wheat fraction, having high concentrations of (glycosyl)ceramides and glycolipids, and enriched in (glycosyl)ceramides by purification (FR-A-91 06336; WO-A-92/21321).

The presence of a high proportion of (glycosyl)ceramides is advantageous due to the fact that ceramides (glycosylated or not) are cell membrane components which contribute to the cell functions. They have been found in the skin, and other vital organs in the human body. Similarly, ceramides (glycosylated or not) have been isolated from plants such wheat, spinach, rice, soya and millet.

For instance, the chemical structure of a glycosylated ceramide consists of a fatty acid, a long aliphatic base such as sphingosine or phytosphingosine, and a sugar moiety such as glucose. The fatty acid is bound to the aliphatic base through an amide bond, while the sugar moiety is bound to the aliphatic base through a glycosidic bond. Ceramides are free of sugar moieties.

Recent studies on the evaluation of the (glycosyl) ceramide properties and particulary on plant ceramides have shown that these compounds are not cytotoxic as not inhibiting cell proliferation,
are highly moisturizing agents for the skin epidermis.
They also exhibit
an anti-radical effect,
an anti-elastase effect as protecting the generation of elastic fibers and collagen for the connective tissue as decribed by Bizot-Foulon V. et al. in Int. J. Cosmetic Science 17, 255–264, 1995.

The potential of ceramides and in particular the plant ones to penetrate the epidermis has been examined both in in vivo and in vitro studies using autopsy skin samples and experimentally regenerated skin. The results indicated that ceramides were found from epidermis to the basal layer and especially in the intracellular space between the keratinocytes, while they did not show any systemic crossing.

Another property of the (glycosyl)ceramides which is of particular interest in the present invention, refers to their carrier properties by enhancing the bioavailability of active compounds to epidermis.

A purified product rich in (glycosyl)ceramides, prepared from wheat and preferably used according to the present invention, is in the form of a beige powder and has the following composition (w/w):

polar lipids (glycolipids+phospholipids+ceramides+glycosylceramides): 70 to 85%;
proteins: 4 to 7%;
apolar lipids: 5 to 15%;
moisture: 1 to 3%.

The extracts of plant ceramides are essentially composed of glycosylceramides and ceramides as defined above, wherein the sphingosine moiety is a phytosphingosine moiety.

According to still another preferred embodiment of the present invention, the hydro-alcoholic gel formulation has the following composition:

wheat prolamines: about 31% w/w;
wheat polar lipids: about 1.3% w/w;
hydro-ethanolic solution (50°): ad 100%.

According to another of its aspects, the invention provides a method for the preparation of the hydro-alcoholic gel formulation described above, which method comprises the steps of:

heating a hydro-ethanolic solution at 42 to 48° C.;
adding to this solution the corresponding amount of prolamine powder, in small portions, under vigorous stirring till a homogeneous dispersion is obtained;
adding to this dispersion the corresponding amount of plant polar lipid powder, possibly with the additives;
stirring the dispersion at 42 to 48° C. for 20 to 40 minutes; and
allowing the mixture to cool at ambient temperature, under gentle stirring.

The prolamine-plant polar lipid association (hereafter "the association") in the form of a film or a patch as proposed in the present invention can be produced in a variety of sizes and thicknesses dependent on the skin/mucosal site to be applied to and the type of treatment to be used.

In preferred embodiments of this invention, the association can further comprise plasticizing agents, which can improve the elastomeric/viscoelastic properties of the prolamines, and active agents known in the art to be used for dermal, transdermal, mucosal or transmucosal administration and also for skin healing and protection, wound healing and hemostasis.

In the other preferred embodiments of this invention, the association can be produced in the form of a film by using an aerosol applicator, or a roller such as employed in the application of a deodorant where the film is formed on the skin as the hydroalcoholic solution evaporates, or alternatively by precasting prior to its application.

Figure 3:
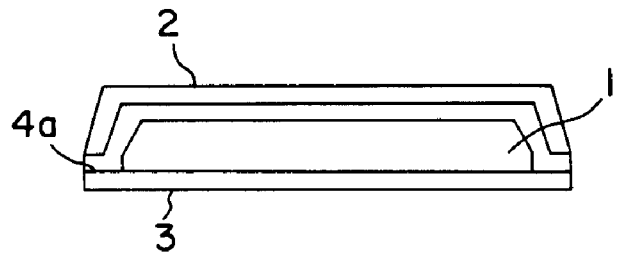
Figure 4:
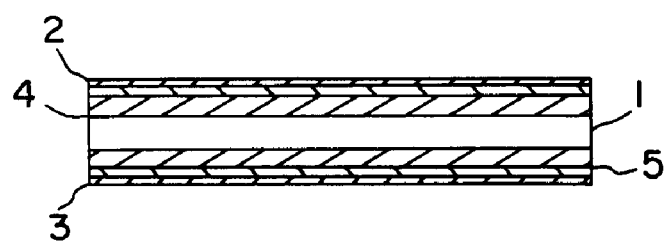
Figure 5:
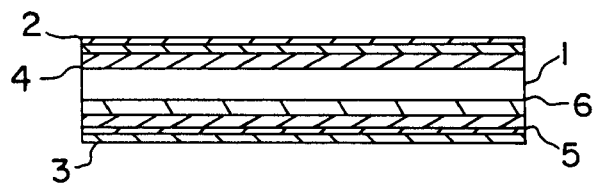

In another embodiment of the present invention, the patch containing the association as presented in FIG. 1, comprises the association as a layer 1, which is suited between a backing film 2 and a removable layer 3. The backing film 2 might be initially laminated with a thin synthetic adhesive layer 4, as presented in FIG. 2, which facilitates the casting of an association layer on it. Similarly, the casting of an association layer can achieved through a peripheral adhesive 4a as shown in FIG. 3. In addition, the removable layer 3 might be also laminated with a thin layer of synthetic adhesive 5 or a porous membrane 6, as presented in FIGS. 4 and 5, respectively, wherein the synthetic adhesive 5 comes directly in contact with the selected area of application after the removable layer 3 is stripped off.

Figure 6:
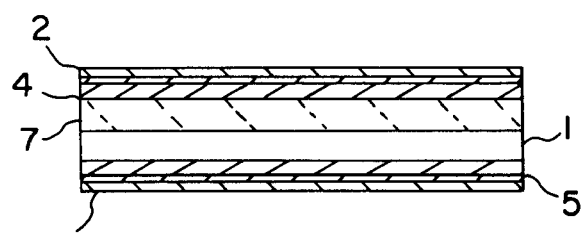

In still another embodiment of the present invention, the association can be formed in a multi-layer system 1-7, containing different concentrations of active agents to act as a gradient system for optimizing the efficacy of the path, as illustrated in FIG. 6.

Figure 2:
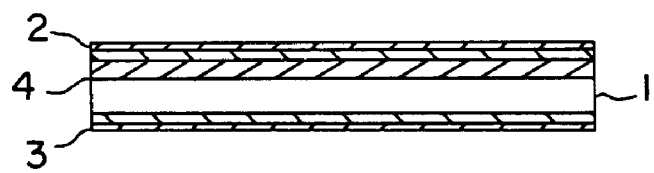

In other embodiments of the present invention, the patches shown in FIGS. 1 and 2 can be prepared without a removable layer 3.

The backing film layer may be made of plastic, fabric, woven or non-woven materials, porous or occlusive. Preferably, the backing film is always breathable for those applications including skin protection and healing, wound healing and hemostasis.

The backing film can be made of any suitable material known in the art such as paper; cellophane; plastic films such as polyethylene, polyester, polyurethane, polyvinyl chloride and polyamide; fabrics and metallic foils which are impermeable and non-reacting with the active substances present in the association layer. The backing film can be composite, transparent, opaque or fleshtoned, or aluminized, or a combination thereof with a thickness ranging from 1 to 5 mils ($1/1000$ of an inch) (about 25 to 130 $\mu$m) and can be formed from any of CoTran™ 9720 (3M), Saranex® (Dow Chemicals), Multilam fleshtoned polyester film 1009 (3M)

or any other material recognized in the art as having the desirable properties.

The removable layer is placed against the surface of the association layer, on the surface opposite to the backing film. The removable layer can be made of materials impermeable to any substance present in the association layer and is easily released prior to the use. The easily removable layer can be made of materials such as polyvinyl chloride, polyester, polyvinylidene chloride, polystyrene, polyethylene, paper etc. coated or not with an adhesive or a membrane.

Preferably the removable layer is made of a natural, high impact polystyrene film (grade code: 10106) sold by REXAM Release or a siliconized polyester film sold by REXAM Release. The thickness of the easily removable layer usually ranges from 3 to 10 mils (about 76 to 250 $\mu$m).

The membranes used for coating the removable layer laminated with a thin layer of synthetic adhesive may be microporous or semipermeable. These membranes can be made of microporous polyethylene film or ethylene vinyl acetate film. Preferably, the membranes are made of CoTran® 9711 and CoTran® 9702 sold by 3M.

The therapeutic agents incorporated in the association layer can be a variety of hydrophilic and hydrophobic agents of any therapeutic category used for systemic or topical treatment such as antimicrobials such as penicillin, tetracycline, erythomycine and the like, analgesics such as morphine, meperidine and the like, antipyretics and antiinflammatory agents such as salicylates, indole derivatives and the like, antispasmodics such as scopolamine, atropine and the like, hormonal agents such as cortisone, cortisol, calcitonin and the like, local anesthetics such as procaine, lidocaine, xylocaine and the like, sympathomimetic drugs such as epinephrine, amphetamine and the like, antiparasitic agents such as metronidazole, fenthion, cythioate and the like, hypoglycemic drugs such as insulin and insulin derivatives and the like, anti-acne agents such as salicylic acid, benzoyl peroxide, retinoic acid and the like, nutritional agents such as vitamins, essential amino acids, essential fats and the like and other beneficial active agents.

Cosmetic agents incorporated in the association layer can be any of anti-hyperpigmentation, anti-blotching, antiaging, eye contour, slimming, anti-cellulite, soothing/sunburn anti-irritating, skin firming and lifting, anti-elastase and anti-collagenase agents, free radical scavengers, seboregulators, hydratives, and AHA ($\alpha$-hydroxy acids) specific products and the like, vitamins and other beneficial active agents.

Active agents used for skin protection and renewal, wound healing and hemostasis can be antimicrobials such as penicillin, tetracycline, erythromycin and the like, anti-inflammatory agents such as salicylates, indole derivatives and the like, hemostatic agents such as negatively charged phospolipids, particulate substances (kaolin) and the like, skin growth agents such as collagenase inhibitors and the like, wound healing agents such as povidone-iodide, hyaluronic acid and its derivatives, mastichinum oil from Pistachia lentiscus var, Chia and the like, and any other compound known in the art and considered efficient for the treatment of conditions mentioned above.

When appropriate, the association carrier system is not processed into a film but the film formation is achieved directly onto the skin site. Therefore, the association carrier system in solution containing all the active substances and other additives is sprayed onto the skin and the film is formed after the evaporation of the solvents.

Before the application of the association film or patch of the invention to a skin site, the skin has to be hydrated using normal saline or water for injection so that the adhesiveness of the association is restored. In case of wounds, and particularly of exuding ones, there is no need of hydration.

In the present invention, the association carrier system in the form of a film or patch is finally sterilized using gamma radiation techniques as described by U.S. and European Pharmacopoeias.

In another embodiment of the present invention, the association film can be folded and encapsulated in a hard capsule for oral controlled delivery of drugs.

Compositions of the present invention can also comprise other pharmaceutically acceptable agents such as solvents, antioxidants, plasticizers, solubilizers, skin permeation enhancers, moisturizers, preservatives, etc. known in the art, as to benefit the properties of the carrier system introduced in the present invention.

In the novel and useful embodiments just described, the method for preparing a film or a patch containing the association comprises admixing the active substances and other additives with the association, this being preferably in a gel form. In case of the patch preparation, in a preferred embodiment, the mixture is casted on a polystyrene layer and then, the system is laminated on a siliconized polyester layer, previously coated with a thin layer of an acrylic adhesive.

The invention is merely illustrated by the following examples which should not be considered to limit the scope of the invention, as these examples and other equivalents thereof will become apparent to those skilled in the art in the light of the present disclosure and drawings. The scope of the invention is defined by the appended claims.

EXAMPLE 1

Preparation of a Powder of Wheat Prolamines (Gliadins), from Ground Whole Wheat

Ground wheat and 99° ethanol, in a proportion of 1:5 (w/w) are introduced into a 1500 liter tank and stirred for 5 to 7 hours, using a propeller mixer. The mixture is then finely filtered.

The delipidated cake thus obtained is extracted with 80° ethanol in a proportion of 1:6 (w/w) in a 1500 liter tank by stirring overnight using a propeller mixer, at a temperature of 28 to 40° C. The mixture is then filtered using a filter press.

The new cake thus obtained is extracted again with 80° ethanol in a proportion of 1:5 (w/w) in a 1500 liter tank by stirring overnight using a propeller mixer, at a temperature of 28 to 40° C. The mixture is then filtered using a filter press.

The filtrates are combined and concentrated under vacuum till the ethanol is completely evaporated. To the concentrate containing a mixture of wheat prolamines and water, cold water in a proportion of 1:3 (v/v) is added. After lefting the above mixture precipitate, a wet paste is obtained.

This wet paste is mixed with acetone in a 1:5 (v/v) ratio, vigorously stirred (about 3000 rpm) for 20 to 40 minutes, and then filtered on a Buchner funnel.

The cake of gliadins thus obtained is rinsed with 3 volumes of acetone, filtered on a Buchner funnel under vacuum, dried in an oven under vacuum, ground and micronized.

A light beige to beige fine powder is thus obtained. It contains 75 to 90% of prolamines (Kjeldahl method) and 1 to 2% of lipids. Its amino acid composition is (% w/w): arginine: 2.7; histidine: 2.3; lysine: 1.1; tyrosine: 3.2; tryptophane: 0.6; phenylalanine: 6.9; cystine: 2.6; threonine: 2.1; serine: 4.9; leucine: 6.5; methionine: 1.7; aspartic acid:

1.3; isoleucine: 5.4; valine: 2.7; glutamic acid: 40.0; glycine: 0.5; alanine: 2.1; proline: 13.4.

EXAMPLE 2

Preparation of a Gel According to the Invention 30 to 35 g of the gliadin powder of Example 1, called hereafter "gliadin", are added in small portions to 70 to 80 g of a hydro-ethanolic solution (50°) heated at 42 to 48° C. under vigorous stirring till a homogeneous dispersion is obtained.

15 to 20 g of the purified wheat (glycosyl)ceramides described above, called hereafter "ceramides", are added to this dispersion. The stirring and the heating at 42 to 48° C. are continued for 20 to 40 minutes. Then, the mixture is allowed to cool at ambient temperature under gentle stirring.

Finally, a light brown to dark brown gel with a viscosity of 800–1200 cp, is obtained, having the following composition (w/w):

gliadin content: 27–30%;
ceramide content: 1–2%.

EXAMPLE 3

Preparation of a Gel According to the Invention, which Contains Glycerol and Sorbitol as Platicizers

Example 3a

A "stock" association gel is prepared as follows:
1. Prepare 604.63 g of a 50% alcoholic solution (EtOH:H$_2$O)
2. Weigh 272.08 g of gliadin powder and 12.09 g of cereal ceramide powder (purity 50%).
3. Add the gliadin and ceramide powders in the alcoholic solution under vigorous agitation at 42–48° C.
4. Weigh seperately 33.25 g of glycerol (purity 99%) and 77.94 g of sorbitol (purity 70%) (proportion 3:7), mix in a beaker to obtain a homogeneous solution.
5. Add the previous solution to the mixture obtained at step 3.

Example 3b

According to another embodiment, a similar gel can be obtained as described in Example 2 above, except that glycerol and sorbitol are added together with the ceramide powder in such proportions that the gel has the following composition (w/w):

prolamine content: 27–30%;
ceramide content: 1–2%;
glycerol content: 2.5–5%;
sorbitol content: 6–9%.

EXAMPLE 4

Preparation of a Gliadin-ceramide Association Patch

The Preparation of a patch comprising a gliadin-ceramide association is described below:

1. Preparation of the Gliadin-ceramide Association Based Mixture

A composition of such a mixture used for the preparation of a device for topical application directly onto the skin is given in Table 1.

TABLE 1

Composition of the mixture

| COMPONENT | QUANTITY % w/w |
|---|---|
| Gel of Example 3 | 89.08 |
| Anti-acne agent | 10.00 |
| Phenonip ® * | 0.45 |
| Potassium Sorbate | 0.05 |
| DL-α-Tocopherol | 0.42 |

* Phenonip is a mixture of phenoxyethanol, methylparaben, ethylparaben, propylparaben and butylparaben.

The preparation of the gliadin mixture is as follows:

Potassium sorbate (0.05 g) is added to a mixture of anti-acne agent (10 g), Phenonip (0.45 g) and DL-α-tocopherol (0.42 g dissolved in 50% ethanol) and the whole is stirred at ambient conditions until all the ingredients are completely dissolved. This mixture is further dissolved in a part of a 89.08 g portion of gel (containing, on a dry basis, 73% of gliadin powder, 3% of ceramide powder, 15% of sorbitol and 9% of glycerol) and stirred for 15 min at ambient conditions, till a homogeneous mixture is obtained. Then, the rest of the gel is added and the mixture is stirred further for 15 min. The system is kept aside for a short time to have the air bubbles completely removed.

2. Casting of a Synthetic Adhesive on the Backing Film

Using an appropriate coating device (square tool Multi Clearance Applicator, sold by BYK gardner) with a 5 mil (about 130 μm) casting gap, a layer of a synthetic adhesive such as DuroTak 87-2353 is coated onto a siliconized polyester film and dried in an oven at 70–75° C. for 15–18 minutes. A low density polyetylene film is then laminated on the synthetic adhesive film. The system is kept aside.

3. Preparation of an Association Coating

Using an appropriate coating device (square tool Multi Clearance Applicator, sold by BYK gardner) with a 5 mil (about 130 μm) casting gap, a layer of the mixture as obtained in Section 1 is coated on the non-siliconized site of a polystyrene film and dried in an oven at 60–62° C. for 10–12 minutes.

The mixture containing laminate is, then, laminated with the system described in Section 2 after the polyethylene film has been removed.

The multi-layer laminate thus obtained is cut to form a device of any desirable size and shape.

Figure 7A:
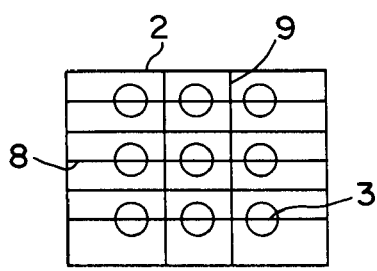
FIGS. 7a and 7b show a set of circular patches in a format that is suitable for prolonged use by the patient.
Figure 7B:
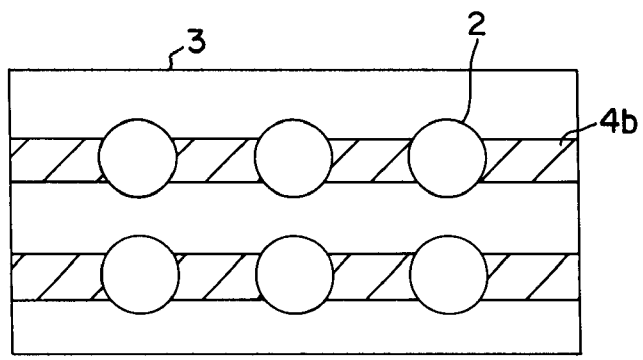

In one embodiment of the present invention, the removable layer is passed through the Flexomaster 1B (sold by ALLIED GEAR) and circular patches of 0.5" (about 1.3 cm) diameter are cut, leaving the removable layer not penetrated. Scoring 8 and perforation 9 lines are simultaneously engraved at perpendicular mode. As shown in FIG. 7a, the perforation lines are engraved in the middle of devices space while the scoring lines are engraved horizontally on the removable layers.

EXAMPLE 5

Preparation of a Gliadin-ceramide Association Patch Containing a Skin Whitening Agent The mixture used in this example has the following composition:

TABLE 2

Composition of the mixture

| COMPONENT | QUANTITY % w/w |
|---|---|
| Gel of Example 3 | 87.00 |
| Etioline[1] | 5.00 |
| Gatuline Whitening[2] | 5.00 |
| Ascorbyl palmitate | 2.00 |
| DL-α-Tocopherol | 1.00 |

[1]Etioline is an African plant extract (Matricarpe of Spermacocea genus), which can inhibit tyrosinase, an enzyme responsible for melanin synthesis.
[2]Gatuline whitening obtained by fermentation of kojic and lactic acids is a tyrosinase inhibitor.

The rest of the procedure remains the same as in Example 4.

EXAMPLE 6

Preparation of a Gliadin-ceramide Association Patch Containing Local Anesthetic

The mixture used in this example has the following composition:

TABLE 3

Composition of the mixture

| COMPONENT | QUANTITY % w/w |
|---|---|
| Gel of Example 3 | 98.80 |
| Lidocaine HCl | 1.00 |
| Chlorhexidine digluconate | 0.20 |

The rest of the procedure remains the same as in Example 4.

EXAMPLE 7

Preparation of a Gliadin-ceramide Association Patch Containing Skin Firming/lifting Agents The mixture used in this example has the following composition:

TABLE 4

Composition of the mixture

| COMPONENT | QUANTITY % w/w |
|---|---|
| Gel of Example 3 | 89.09 |
| Gatuline lifting[1] | 3.00 |
| Retinyl palmitate | 2.00 |
| Gatuline RC[2] | 5.00 |
| DL-α-Tocopherol | 0.17 |
| Transcutol | 0.74 |

[1]Gatuline lifting is a plant extract containing flavonoids, tannins and a proteic fraction having similar properties to bovine serum albumine.
[2]Gatuline RC is a Beech tree buds extract containing flavonoids, peptides such as phytostimulins and others.

The rest of the procedure remains the same as in Example 4.

EXAMPLE 8

Preparation of a Gliadin-ceramide Association Patch Containing a Keratolytic Agent The mixture used in this example has the following composition:

TABLE 5

Composition of the mixture

| COMPONENT | QUANTITY % w/w |
|---|---|
| Gel of Example 3 | 99.50 |
| Salicylic acid | 0.50 |

The rest of the procedure remains the same as in Example 4.

EXAMPLE 9

Preparation of a Gliadin-ceramide Association Patch for Skin Renewal

A composition of the mixture used for the preparation of a patch for topical application onto the skin is given in Table 6.

TABLE 6

Composition of the mixture

| COMPONENT | QUANTITY % w/w |
|---|---|
| Gel of Example 3 | 98.58 |
| Collagenase inhibitor | 0.20 |
| Phenonip ® * | 0.75 |
| Potassium Sorbate | 0.05 |
| DL-α-Tocopherol | 0.42 |

* Phenonip is a mixture of phenoxyethanol, methylparaben, ethylparaben, propylparaben and butylparaben The rest of the procedure remains the same as in Example 4.

EXAMPLE 10

Preparation of a Gliadin-ceramide Association Patch for Wound Healing

A composition of the mixture used for the preparation of a patch for topical application onto the skin is given in Table 7.

TABLE 7

Composition of the mixture

| COMPONENT | QUANTITY % w/w |
|---|---|
| Gel of Example 3 | 92.58 |
| Mastichinum oil | 5.00 |
| α-Bisabolol | 1.20 |
| Phenonip ® | 0.75 |
| Potassium Sorbate | 0.05 |
| D,L α-Tocopherol | 0.42 |

The rest of the procedure remains the same as in Example 4.

Another composition for wound healing is presented in the following Table:

TABLE 8

Composition of the mixture

| COMPONENT | QUANTITY % w/w |
|---|---|
| Gel of Example 3 | 95.00 |
| Povidone iodide | 5.00 |

EXAMPLE 11

Preparation of a Gliadin-ceramide Association Patch Containing a Skin Whitening Agent The gliadin mixture used in this example has the following composition:

TABLE 9

Composition of the mixture

| COMPONENT | QUANTITY % w/w (on a dry basis) |
|---|---|
| Gliadin powder | 59.87 |
| Ceramide powder | 2.66 |
| Sorbitol | 17.14 |
| Glycerol | 7.33 |
| Etioline | 5.00 |
| Gatuline Whitening | 5.00 |
| Ascorbyl palmitate | 2.00 |
| DL-α-Tocopherol | 1.00 |

The rest of the procedure remains the same as in Example 4.

EXAMPLE 12

Preparation of a Gliadin-ceramide Association Patch Containing Local Anesthetic

The mixture used in this example has the following composition:

TABLE 10

Composition of the mixture

| COMPONENT | QUANTITY % w/w (on a dry basis) |
|---|---|
| Gliadin powder | 68.00 |
| Ceramide powder | 3.00 |
| Sorbitol | 19.50 |
| Glycerol | 8.30 |
| Lidocaine HCl | 1.00 |
| Chlorhexidine digluconate | 0.20 |

The rest of the procedure remains the same as in Example 4.

EXAMPLE 13

Preparation of a Gliadin-ceramide Association Patch Containing Skin Firming/Lifting Agents The gliadin mixture used in this example has the following composition:

TABLE 11

Composition of the mixture

| COMPONENT | QUANTITY % w/w (on a dry basis) |
|---|---|
| Gliadin powder | 61.31 |
| Ceramide powder | 2.73 |
| Sorbitol | 17.55 |
| Glycerol | 7.50 |
| Gatuline lifting | 3.00 |
| Retinyl palmitate | 2.00 |
| Gatuline RC | 5.00 |
| DL-α-Tocopherol | 0.17 |
| Transcutol | 0.74 |

The rest of the procedure remains the same as in Example 4.

EXAMPLE 14

Preparation of a Gliadin-ceramide Association Patch Containing a Keratolytic Agent The mixture used in this example has the following composition:

TABLE 12

Composition of the mixture

| COMPONENT | QUANTITY % w/w (on a dry basis) |
|---|---|
| Gliadin powder | 68.48 |
| Ceramide powder | 3.04 |
| Sorbitol | 19.60 |
| Glycerol | 8.38 |
| Salicylic acid | 0.50 |

The rest of the procedure remains the same as in Example 4.

EXAMPLE 15

Preparation of a Gliadin-ceramide Association Patch for Skin Renewal

A composition of the mixture used for the preparation of a patch for topical application onto the skin is given in Table 13.

TABLE 13

Composition of the mixture

| COMPONENT | QUANTITY % w/w (on a dry basis) |
|---|---|
| Gliadin powder | 67.84 |
| Ceramide powder | 3.02 |
| Sorbitol | 19.42 |
| Glycerol | 8.30 |
| Collagenase inhibitor | 0.20 |
| Phenonip ® | 0.75 |
| Potassium Sorbate | 0.05 |
| D,L-α-Tocopherol | 0.42 |

The rest of the procedure remains the same as in Example 4.

EXAMPLE 16

Preparation of a Gliadin-ceramide Association Patch for Wound Healing

A composition of the mixture used for the preparation of a patch for topical application onto the skin is given in Table 14.

TABLE 14

Composition of the mixture

| COMPONENT | QUANTITY % w/w (on a dry basis) |
|---|---|
| Gliadin powder | 63.71 |
| Ceramide powder | 2.83 |
| Sorbitol | 18.24 |
| Glycerol | 7.80 |
| Mastichinum oil | 5.00 |
| α-Bisabolol | 1.20 |
| Phenonip ® | 0.75 |
| Potassium Sorbate | 0.05 |
| D,L α-Tocopherol | 0.42 |

The rest of the procedure remains the same as in Example 4.

Another composition for wound healing is presented in the following Table:

TABLE 15

Composition of the mixture

| COMPONENT | QUANTITY % w/w (on a dry basis) |
|---|---|
| Gliadin powder | 65.38 |
| Ceramide powder | 2.91 |
| Sorbitol | 18.71 |
| Glycerol | 8.00 |
| Povidone iodide | 5.00 |

What is claimed is:

1. A patch comprising a backing film, a removable layer and an association layer between the backing film and the removable layer; wherein the association layer comprises prolamine and plant polar lipid, wherein the prolamine and the plant polar lipid are provided in proportions sufficient to enable formation of a stable patch, and wherein the patch exhibits skin adhesion properties.

2. The patch according to claim 1, wherein the association layer is formed using a hydro-ethanolic gel comprising 20 to 40% w/w prolamine and 0.1 to 5% w/w plant polar lipid.

3. The patch according to claim 2; wherein the association layer is formed using a hydro-ethanolic gel comprising 31% w/w prolamine, 1.3% w/w plant polar lipid; wherein the prolamine comprises wheat prolamines and the plant polar lipid comprises wheat polar lipids.

4. The patch according to claim 1, wherein the association layer further comprises a plasticizing agent.

5. The patch according to claim 1; wherein the association layer is formed using a hydro-ethanolc gel comprising 27 to 30% w/w prolamine, 1–2% w/w plant polar lipid, 2.5–5% w/w glycerol and 6–9% sorbitol; wherein the plant polar lipid comprises ceramide.

6. The patch according to claim 1, wherein the association layer further comprises an active substance selected from the group consisting of therapeutic agents, cosmetic agents and active agents.

7. The patch according to claim 6, wherein the active substance is a therapeutic agent selected from the group consisting of systemic or topical treatment agents including penicillin, tetracycline and erythomycin; analgesics including morphine and meperidine; antipyretics and antiinflammatory agents including salicylates and indole derivatives; antispasmodics including scopolamine and atropine; hormonal agents including cortisone, cortisol and calcitonin; local anesthetics including procaine, lidocaine and xylocaine; sympathomimetic drugs including epinephrine and amphetamine; antiparasitic agents including metronidasole, fenthion and cythioate; hypoglycemic drugs including insulin and insulin derivatives; anti-acne agents including salicylic acid, benzoyl peroxide and retinoic acid; nutritional agents including vitamins, essential amino acids and essential fats.

8. The patch according to claim 1, wherein the association layer further comprises an active substance selected from the group consisting of anti-hyperpigmentation agents, anti-blotching agents, anti-aging agents, eye contour agents, slimming agents, anti-cellulite agents, soothing/sunburn anti-irritating agents, skin firming and lifting agents, anti-elastase agents and anti-collagenase agents, free radical scavengers; seboregulators, hydratives, alpha-hydroxy acids and vitamins.

9. The patch according to claim 1, wherein the association layer further comprises an active substance selected from the group consisting of antimicrobials including penicillin, tetracycline and erythromycin; anti-inflammatory agents including salicylates and indole derivatives; hemostatic agents including negatively charged phospholipids and kaolin; skin growth agents including collagenase inhibitors and wound healing agents including povidone-iodide, hyaluronic acid and its derivatives, mastichinum oil from *Pistachia lentiscus* var and Chia.

10. The patch according to claim 6, wherein the patch comprises at least two association layers, wherein the association layers contain different concentrations of active substances.

11. The patch according to claim 1, wherein the prolamine comprises gliadin.

12. The patch according to claim 1, wherein the plant polar lipid comprises a high proportion of ceramides and glycosylceramides.

13. The patch according to claim 12, wherein the plant polar lipid comprises cereal polar lipid.

14. The patch according to claim 13, wherein the cereal polar lipid comprises wheat polar lipid.

15. A method of making a hydro-alcoholic gel formulation for use in preparing the association layer of claim 1, comprising:
    (a) heating a hydro-ethanolic solution to 42–48° C.;
    (b) adding prolamine to the hydro-ethanolic solution under vigorous stirring to form a dispersion;
    (c) adding plant polar lipid to the dispersion;
    (d) stirring the dispersion while maintaining the temperature at 42–48° C. for 20 to 40 minutes; and,
    (e) allowing the dispersion to cool under ambient conditions with gentle stirring.

16. The method of claim 15, wherein additives are added to the dispersion along with the plant polar lipid.

17. A method for administering an active substance to a human, comprising forming a patch in situ on the skin of the human, wherein the patch comprises an association layer comprising a prolamine and a plant polar lipid.

18. The method of claim 17, wherein the wherein the association layer is formed using a hydro-ethanolic gel comprising 20 to 40% w/w prolamine and 0.1 to 5% w/w plant polar lipid.

19. The method of claim 17; wherein the association layer is formed using a hydro-ethanolic gel comprising 31% w/w prolamine, 1.3% w/w plant polar lipid; wherein the prolamine comprises wheat prolamines and the plant polar lipid comprises wheat polar lipids.

20. The method of claim 17; wherein the association layer is formed using a hydro-ethanolic gel comprising 27 to 30% w/w prolamine, 1–2% w/w plant polar lipid, 2.5–5% w/w glycerol and 6–9% sorbitol; wherein the plant polar lipid comprises ceramide.

21. The method of claim 17, wherein the active substance is selected from the group consisting of therapeutic agents, cosmetic agents and active agents.

22. The method of claim 17, wherein the active substance is selected from the group consisting of systemic or topical treatment agents including penicillin, tetracycline and erythomycin; analgesics including morphine and meperidine; antipyretics and antiinflammatory agents including salicylates and indole derivatives; antispasmodics including scopolamine and atropine; hormonal agents including cortisone, cortisol and calcitonin; local anesthetics including procaine, lidocaine and xylocaine; sympathomimetic drugs including epinephrine and amphetamine; antiparasitic agents including metronidasole, fenthion and cythioate; hypoglycemic drugs including insulin and insulin derivatives; anti-acne agents including salicylic acid, benzoyl peroxide and retinoic acid; nutritional agents including vitamins, essential amino acids and essential fats.

23. The method of claim 17, wherein the active substance is selected from the group consisting of anti-hyperpigmentation agents, anti-blotching agents, anti-aging agents, eye contour agents, slimming agents, anti-cellulite agents, soothing/sunburn anti-irritating agents, skin firming and lifting agents, anti-elastase agents and anti-collagenase agents, free radical scavengers; seboregulators, hydratives, alpha-hydroxy acids and vitamins.

24. The method of claim 17, wherein the active substance is selected from the group consisting of antimicrobials including penicillin, tetracycline and erythromycin; anti-inflammatory agents including salicylates and indole derivatives; hemostatic agents including negatively charged phospholipids and kaolin; skin growth agents including collagenase inhibitors and wound healing agents including povidone-iodide, hyaluronic acid and its derivatives, mastichinum oil from *Pistachia lentiscus* var and Chia.

25. The method of claim 17, wherein the prolamine comprises gliadin.

26. The method of claim 17, wherein the plant polar lipid comprises a high proportion of ceramides and glycosylceramides.

27. The method of claim 17, wherein the plant polar lipid comprises cereal polar lipid.

28. The method of claim 17, wherein the cereal polar lipid comprises wheat polar lipid.

\* \* \* \* \*